United States Patent [19]
Esfandiari et al.

[11] Patent Number: 5,658,868
[45] Date of Patent: Aug. 19, 1997

[54] MOISTURIZING BODY SOAP AND SHAMPOO

[76] Inventors: Saed Esfandiari, 1290 Verdon Dr., Dunwoody, Ga. 30338; Lonzell Graham, 302 Vesper Cir., Mauldin, S.C. 29662

[21] Appl. No.: 681,867

[22] Filed: Jul. 29, 1996

Related U.S. Application Data

[60] Provisional application No. 60/001,709, Jul. 31, 1995.
[51] Int. Cl.$^6$ ........................................ C11D 1/94
[52] U.S. Cl. ............... 510/155; 510/126; 510/127; 510/156; 510/450; 510/463
[58] Field of Search ........................... 510/127, 126, 510/155, 156, 447, 450, 463, 141; 8/405, 435

[56] References Cited

U.S. PATENT DOCUMENTS

| | | | |
|---|---|---|---|
| 4,490,355 | 12/1984 | Desai | 510/121 |
| 4,654,207 | 3/1987 | Preston | 510/424 |
| 5,109,127 | 4/1992 | Sekiguchi et al. | 510/122 |
| 5,352,386 | 10/1994 | Rahman et al. | 252/548 |
| 5,540,853 | 7/1996 | Trinh et al. | 510/129 |
| 5,580,849 | 12/1996 | Dyet et al. | 510/427 |

*Primary Examiner*—Paul Lieberman
*Assistant Examiner*—Caroline L. Dusheck
*Attorney, Agent, or Firm*—Michael I. Kroll

[57] ABSTRACT

A composition for a moisturizing soap/shampoo contains alpha olefin sulfonate, sodium sulfoccinate ester of alkanolamide, lauroamphocarboxyglycinate, coconut amide, glycol disterate, aloe vera, wheat germ oil and water. Optionally, the composition can contain JoJoba oil, colorants, fragrances and/or preservatives.

11 Claims, No Drawings

MOISTURIZING BODY SOAP AND SHAMPOO

This application claims the benefit of U.S. Provisional application Ser. No. 60/001,709, filed Jul. 31, 1995.

BACKGROUND OF THE INVENTION

1. Field of the Invention

The instant invention relates generally to a soap composition for cleansing and conditioning skin and hair.

2. Description of the Prior Art

The use of natural soap to clean the hair (shampoo) and to clean the skin (body soap) dates back over 2000 years. The process for making soap generally relies on a process known as saponification. Specifically, mixing fat with alkali will cause the fat to hydrolyze, or split, into a mixture of fatty acids and glycerin. In commercial processes, the glycerin is removed for use in any number of other applications. The fatty acids are then neutralized, commonly by addition of caustic soda, to form the raw soap. The raw soap can then be modified for commercial use, for example, by the addition of various adjuncts, for example, colorants, perfumes, moisturizers and preservatives.

The neutralization of the fatty acids with soda results in what is known as a sodium soap. One of the most common problems associated with sodium soaps is that they tend to cause precipitate-formation from hard (mineral-rich) water. These precipitates are undesireable because they are difficult to rinse from the hair and skin and can also leave stubborn deposits in sinks, tubs and shower stalls.

Another difficulty with fatty acid sodium soaps and shampoos derives from the general incompatibility between the cleansing and the conditioning components. The most common solution has been to use two separate products, for example, a cleansing shampoo followed by a conditioning agent. For convenience, however, it is preferable to have the cleansing and conditioning components in a single formulation. Unfortunately, most combination shampoo/conditioners do not perform as well as separate formulations.

SUMMARY OF THE INVENTION

It is, therefore, an object of the present invention to provide a bar soap which is effective for both cleansing and conditioning, that is, a single stable formulation containing effective cleansing agents and conditioning/moisturizing agents.

An additional object is to provide a bar soap which can be used either as a body soap or as a shampoo for hair.

A further object is to provide a bar soap which can be produced at a reasonable commercial cost.

Another object is to provide a bar soap which can be used on a wide variety of skin and hair types, for example, oily, normal, dry, colored, permed, etc.

The foregoing and related objects are accomplished by use of a special composition containing a mixture of Alpha olefin sulfonate, sodium sulfoccinate ester of alkanolamide, lauroamphocarboxyglycinate, coconut amide, glycol disterate, aloe vera, wheat germ oil and water.

DETAILED DESCRIPTION OF THE PREFERRED EMBODIMENTS

A detailed description is herein given of the present invention as a cleansing and conditioning-soap for skin and hair.

It has been found that the present formulation provides a bar soap which accomplishes all of the above-recited objects of the invention. The table below shows the general range, on a weight percent basis, of the formulation.

TABLE 1

| Ingredient | Recommended Range (wt %) |
| --- | --- |
| Alpha olefin sulfonate | 7.0–16.0 |
| Sodium sulfoccinate Ester of alkanolamide | 18.5–33.3 |
| Lauroamphocarboxyglycinate | 15.1–18.2 |
| Coconut amide | 1.2–5.5 |
| Glycol disterate | 0.5–3.5 |
| Aloe vera | 0.5–4.0 |
| Wheat germ oil | 0.3–1.5 |
| Water | 8.2–56.9 |

It will be readily appreciated that in addition to the ingredients listed above, other additives can be routinely added. Examples include preservatives, colorants, fragrances, pH modifiers/buffers, oils such as JoJoba oil, and various other modifiers and stabilizers. These adjuncts are generally added in fairly small amounts, for example, preservatives generally constitute 0.01 to 0.1 weight percent of the final composition, while fragrances and colorants generally constitute significantly less than 1 weight percent of the final composition. Furthermore, the composition can contain colorants for changing or maintaining hair color.

Example 1, below, illustrates the preparation of a bar soap formulation according to the instant invention. In addition to the ingredients listed above, the following adjuncts were added (on a weight percent basis).

| JoJoba oil | 0.1–3.0 |
| --- | --- |
| Preservative | 0.01–0.1 |
| Fragrance | 0.02–0.2 |
| Colorant | 0.01–0.3 |

EXAMPLE 1

In a stainless steel mixing kettle, the various components were mixed as described below, with constant agitation.

Step 1. Add batch water and heat to 85°–90° F.

Step 2. Add alpha olefin sulfonate and coconut amide. Mix for 9–15 minutes.

Step 3. Add lauroamphocarboxyglycinate, aloe vera oil, wheat germ oil and JoJoba oil. Mix for 5–8 minutes.

Step 4. Add citric acid solution and adjust pH to between 6.1 and 6.5.

Step 5. Add preservative, colorant and fragrance. Continue mixing for 10 minutes, maintaining the batch temperature between about 85° F. and 90° F.

Step 6. Pour soap into molds. Allow to cool to room temperature to form a solid soap bar.

It will readily be understood that each of the elements described herein, or two or more together, may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the composition illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A soap bar composition comprising about 7 to 16 percent by weight of alpha olefin sulfonate, about 18 to about 33 percent by weight of sodium sulfoccinate ester of alkanolamide, about 15 to 29 percent by weight of lauroamphocarboxyglycinate, about 1.2 to about 5.5 percent by weight of coconut amide, about 0.5 to about 3.5 percent by weight of glycol disterate, about 0.5 to about 4.0 percent by weight of aloe vera, about 0.5 to about 1.5 percent by weight of wheat germ oil and the remainder water.

2. A composition as defined in claim 1, further comprising JoJoba oil.

3. A composition as defined in claim 1, further comprising a preservative.

4. A composition as defined in claim 1, further comprising a colorant.

5. A composition as defined in claim 1, further comprising a fragrance.

6. A composition as defined in claim 3, further comprising a colorant and a fragrance.

7. A composition according to claim 2, further comprising a preservative, a colorant and a fragrance.

8. A composition according to claim 6, having the relative proportions:

Alpha olefin sulfonate, about 7 to about 16 weight percent;

Sodium sulfoccinate ester of alkanolamide, about 18 to about 33 weight percent;

Lauroamphocarboxyglycinate, about 15–29 weight percent;

Coconut amide, about 1.2 to about 5.5 weight percent;

Glycol disterate, about 0.5 to about 3.5 weight percent;

Aloe vera, about 0.5 to about 4.0 weight percent;

Wheat germ oil, about 0.3 to about 1.5 weight percent;

JoJoba oil, about 0.1 to about 3.0 weight percent;

Preservative, about 0.01 to about 0.1 weight percent;

Fragrance, about 0.02 to about 0.2 weight percent;

Colorant, about 0.01 to about 0.3 weight percent; and

Water, remainder.

9. A composition as defined in claim 1, wherein said composition is a body soap.

10. A composition as defined in claim 1, wherein said composition is a shampoo.

11. A composition as defined in claim 10 further comprising a hair colorant.

* * * * *